US008715305B2

(12) United States Patent
Pate et al.

(10) Patent No.: US 8,715,305 B2
(45) Date of Patent: May 6, 2014

(54) MAGNETIC VENTRICULAR CONNECTOR

(75) Inventors: Thomas D. Pate, Austin, TX (US);
Jeffrey R Gohean, Austin, TX (US);
Raul G. Longoria, Austin, TX (US);
Richard W. Smalling, Houston, TX (US)

(73) Assignee: The Board of Regents of the University of Texas Systems, Austin, TX (US)

( * ) Notice: Subject to any disclaimer, the term of this patent is extended or adjusted under 35 U.S.C. 154(b) by 28 days.

(21) Appl. No.: 13/224,011

(22) Filed: Sep. 1, 2011

(65) Prior Publication Data

US 2012/0059398 A1 Mar. 8, 2012

Related U.S. Application Data

(60) Provisional application No. 61/379,946, filed on Sep. 3, 2010.

(51) Int. Cl.
*A61B 17/11* (2006.01)
(52) U.S. Cl.
USPC ............. 606/153; 606/108; 600/16; 604/533
(58) Field of Classification Search
USPC ............. 606/153–156, 151, 108; 128/202.27; 285/9.1; 604/533, 288.01; 623/3.26; 600/16–17
See application file for complete search history.

(56) References Cited

U.S. PATENT DOCUMENTS

| 4,004,298 | A | 1/1977 | Freed |
| 5,041,131 | A | 8/1991 | Nagase |
| 5,326,373 | A | 7/1994 | Nagase |
| 5,344,443 | A * | 9/1994 | Palma et al. ................. 623/3.14 |
| 6,035,856 | A | 3/2000 | LaFontaine et al. |
| 6,390,098 | B1 | 5/2002 | LaFontaine et al. |
| 6,565,581 | B1 | 5/2003 | Spence et al. |
| 6,732,501 | B2 | 5/2004 | Yu et al. |
| 6,884,251 | B2 | 4/2005 | Spence et al. |
| 7,077,801 | B2 | 7/2006 | Haverich |
| 7,431,727 | B2 * | 10/2008 | Cole et al. ..................... 606/153 |
| 7,493,154 | B2 | 2/2009 | Bonner et al. |
| 7,938,841 | B2 | 5/2011 | Sharkawy et al. |
| 2004/0082850 | A1 | 4/2004 | Bonner et al. |
| 2006/0184088 | A1 | 8/2006 | Van Bibber et al. |
| 2008/0294251 | A1 * | 11/2008 | Annest et al. .................. 623/3.1 |
| 2009/0137900 | A1 | 5/2009 | Bonner et al. |
| 2010/0160719 | A1 * | 6/2010 | Kassab et al. ................... 600/37 |

* cited by examiner

*Primary Examiner* — Julian W Woo
*Assistant Examiner* — Shaun L David
(74) *Attorney, Agent, or Firm* — Streets & Steele; Patrick K. Steele; Jeffrey L. Streets

(57) ABSTRACT

A magnetic coupling for connecting a cannula to the apex of a ventricle comprising a first member having a first orifice, a first magnetic material attached to the first member, a means for attaching a cannula to the first member, a second member having a second orifice, a second magnetic material attached to the second member, a means for attaching the second member to a ventricle, so that when the first magnet is placed in proximity to the second magnet the first member and second member are held substantially concentric by magnetic force to allow for the communication of fluid between the first and second orifices.

20 Claims, 13 Drawing Sheets

MAGNETIC VENTRICULAR CONNECTOR

CROSS-REFERENCE TO RELATED APPLICATION

This application claims the priority of U.S. Provisional Application No. 61/379,946 filed on Sep. 3, 2010, the disclosure of which is incorporated herein by reference for all purposes.

FIELD OF THE INVENTION

Embodiments of the present invention generally relate to securing the aperture of a first tube to a second aperture with magnets. More specifically, embodiments of the present invention relate to connecting the aperture of a cannula to a ventricle, pump inflow or outflow orifice, or a secondary cannula so that fluid can flow freely without substantial leakage. The time to connect and disconnect the fluid connection is substantially reduced.

DESCRIPTION OF RELATED ART

In the field of cardiac mechanical circulatory support, the use of cannulas for transporting fluids is necessary. It is often required to fasten the open end of one cannula to a secondary orifice so that fluid can be transported without leakage or the entrainment of air. Given the limited visibility and maneuverable space during surgery, it is desirable for the connection of a cannula to its desired destination to be simple, fast, and reversible with minimal fluid loss, leakage, or air aspiration.

Ventricular assist devices are used clinically for the treatment of end-stage heart failure. In most of these devices, blood enters the device through an inflow tube, which is inserted into the ventricular cavity while the patient is on cardiopulmonary bypass. A sewing ring is usually attached to the ventricular apex of the heart and the inflow tube of a blood pump is inserted through the sewing ring and into the ventricle. The blood pump is then secured to the sewing ring by placing a ligature, or tie, around the inflow tube of the pump and the sewing ring and tightening them together. A polymeric band can also be placed around the sewing ring collar and tightened down on the inflow tube. By this method, an adequate seal can be made and the pump inflow tube is held in place. However, this method makes it difficult to change the orientation of the inflow tube, or if necessary, to remove the inflow tube from the ventricle. Another connection device makes use of a metallic split ring or c-clamp attached to the sewing ring that clamps and secures an inserted inflow tip when a screw spanning the gap in the split ring is tightened with a wrench. Placing and tightening a polymeric band and ligatures around the inflow tube or locating and tightening a set screw can be difficult within the confined space of the thorax and comprises extra steps in the implant or explant process. Due to the time to complete the aforementioned steps, most ventricular assist devices use partial or total cardiopulmonary bypass support for ventricular apex cannulation, which substantially increases surgical time and can further compromise cardiac performance in patients who have acute heart failure. Avoiding partial or total cardiopulmonary bypass support allows patients to avoid post bypass surgery cognitive dysfunction which has been associated with significant permanent reduction in mental capacity. Patients often suffer memory loss, experience sleep disturbances, suffer mood swings, lose intellectual acuity and some develop persistent depression. These neurocognitive function effects are colloquially referred to as "pump head" and have even spurred the development of beating-heart bypass technology, which circumvents the need for a machine to circulate blood. Off-pump surgery is sometimes referred to as "executive bypass".

Achieving proper alignment of the inflow cannula inside of the ventricle is critical to pumping performance and safety. Improper inflow tip orientation, including improper penetration depth, location, or angle, can result in the inflow tip impinging on or directed towards an endocardial surface or other structures inside of the ventricle. Poor orientation frequently results in suction of the inner heart wall onto the inflow tip during pump operation, which can result in damage to the ventricular wall in the form of bruising or cutting. Improper orientation may also cause thrombus formation around the inflow tip that may embolize or grow to occlude the inflow orifice. Anatomical variability or pathological conditions can result in unpredictable location of known ventricular features, such as papillary muscles and chordae, making it very difficult to know what the inflow tip will encounter upon insertion. In general, the orientation of the inflow tip is selected by locating the apical dimple of the ventricle and attempting to orient the inflow tip towards the mitral valve by estimating the direction of the ventricular septum. A sewing ring is then sewn onto the heart along the chosen axis. Achieving consistently appropriate alignment remains difficult due to the inability to visualize what the inflow tip will encounter prior to attachment of the sewing ring and inserting the tip.

Presently there are no connectors for attachment to a heart that use a reversible magnetic securing mechanism that automatically secures the inflow tip to the ventricle in a simple one-handed step that can be performed blindly, within seconds, and without the use of cardiopulmonary bypass. There are also no balloon alignment catheters for visualizing the shape and orientation of an inflow tip prior to attachment of a sewing ring, which additionally can be used to align a sewing ring to the axis of the balloon catheter.

U.S. Pat. Nos. 6,732,501 and 4,004,298 provide exemplary procedural or other details and are specifically incorporated herein by reference. The prior art also includes U.S. Pat. Nos. 5,041,131, 5,326,373, 7,077,801 and 7,938,841, and Publication 2006/0184088.

The disadvantages of the prior art are overcome by the present invention, an improved magnetic ventricular connector is hereinafter disclosed.

SUMMARY OF THE INVENTION

Certain embodiments comprise a magnetic connector for attaching a cannula to a ventricle, the connector comprising a first member containing a first orifice, a first magnetic material attached to the first member, means for attaching a cannula to the first member, a second member containing a second orifice, a second magnetic material attached to the second member, and means for securing the second member to a ventricle, so that when the first magnet is placed in proximity to the second magnet, the first member and second member are held substantially concentric and in proximity by magnetic force in order to allow for the transfer of fluid.

It is an object of the present invention to provide an easy to use quick connect and disconnect device for connecting a cannula to a patient's heart.

It is another object of the present invention to provide a device that allows for the cannulation of the heart without the use of cardiopulmonary bypass, thereby decreasing risk to the patient, surgical time and costs.

It is another object of the present invention to provide a device that provides a substantial seal in the connection of a cannula to a heart and allows for easy rotation of the orientation of a tube of a blood pump, after insertion into a heart.

These and further features and advantages of the present invention will become apparent from the following detailed description, wherein reference is made to the figures in the accompanying drawings.

DETAILED DESCRIPTION OF PREFERRED EMBODIMENTS

Figure 1:
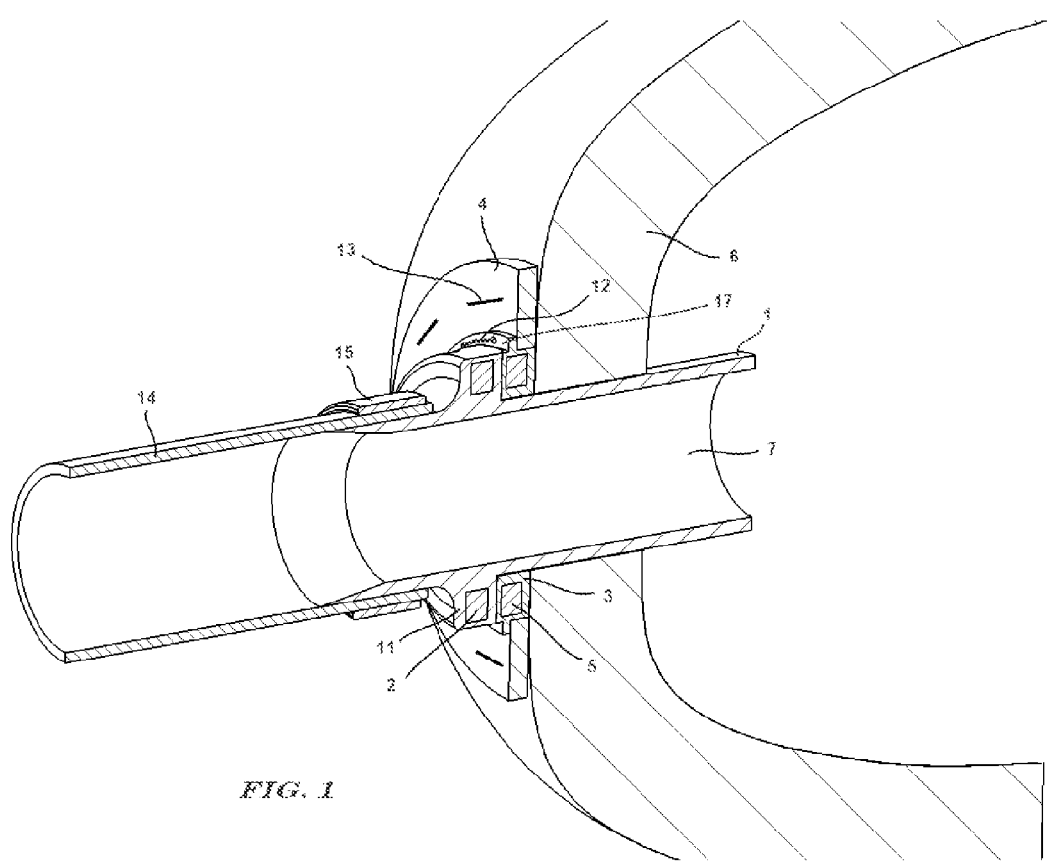
FIG. 1 is a perspective sectional view of the first member assembled onto the second member with the second member attached to the heart.

In the FIG. 1 embodiment, the first member 1 may be comprised of a titanium inflow tip and a flange 11. The flange encapsulates the first magnetic material 2 in a sealed compartment. The first magnetic material may be a permanent magnet or magnetically permeable material, such as steel. One technique for connecting the first member to a cannula 14 is by securing the cannula 14 to the distal side of the inflow tip with a plurality of ligatures that constrict the cannula 14 into grooves in the first member 1. It will be understood that, while some disclosures relating to instruments for use in treating the heart use the term "proximal" as meaning closest to or close to a medical practitioner or user of the instrument and the term "distal" as meaning farthest from or farther from the medical practitioner or user of the instrument, those terms, as they are used herein, describe a relationship to the center of the heart. As used herein, therefore, the term "proximal" means closest or closer to the center of the heart and the term "distal" means farthest from or farther from the center of the heart, which may be outside the heart. For example, an inflow tip inserted through the heart wall to deliver fluid into a chamber of the heart has a proximal end, where the delivered fluid emerges within the heart chamber, and a distal end that is outside of the heart wall and likely to be connected to a fluid supply conduit. Another technique for securing the cannula 14 to the distal side of the inflow tip involves a graft compression band 15, as shown in FIG. 1. The second member 3 may be comprised of a titanium ring with a flange. The second member flange 17 may include a plurality of holes, as shown more clearly in FIG. 2. A sewing cuff or other attachment ring 4 is attached to the flange 17 of the second member 3 via ligatures 12 that thread through the sewing cuff and holes. The attachment ring 4 serves as an attachment device for attaching the second member to the apex of the ventricle, e.g., using sutures 13. Since the outer structure of the heart may vary, the attachment ring 4 is preferably flexible to substantially conform to the exterior of the heart, and may be made from various felt-like materials. The second magnetic material 5 may be a permanent magnet or a magnetically permeable material that is encapsulated by the titanium ring of the second member 3. During connection, the titanium inflow tip 1 is inserted through the orifice in the second member 3 and translated into the ventricle until the first and second magnets reach a predetermined displacement. The first and second magnets are oriented so that they attract each other with substantial force at the predetermined displacement to prevent significant movement of the first member with respect to the second member. In this fashion, a cannula can easily be attached and secured to a ventricle by sliding the inflow tip 1 through the orifice in the second member, with the magnets conjoining the first and second members without the need for any extra steps. All fluid is contained within the flow path in the first member, and the second member is not in contact with the fluid.

Figure 2:
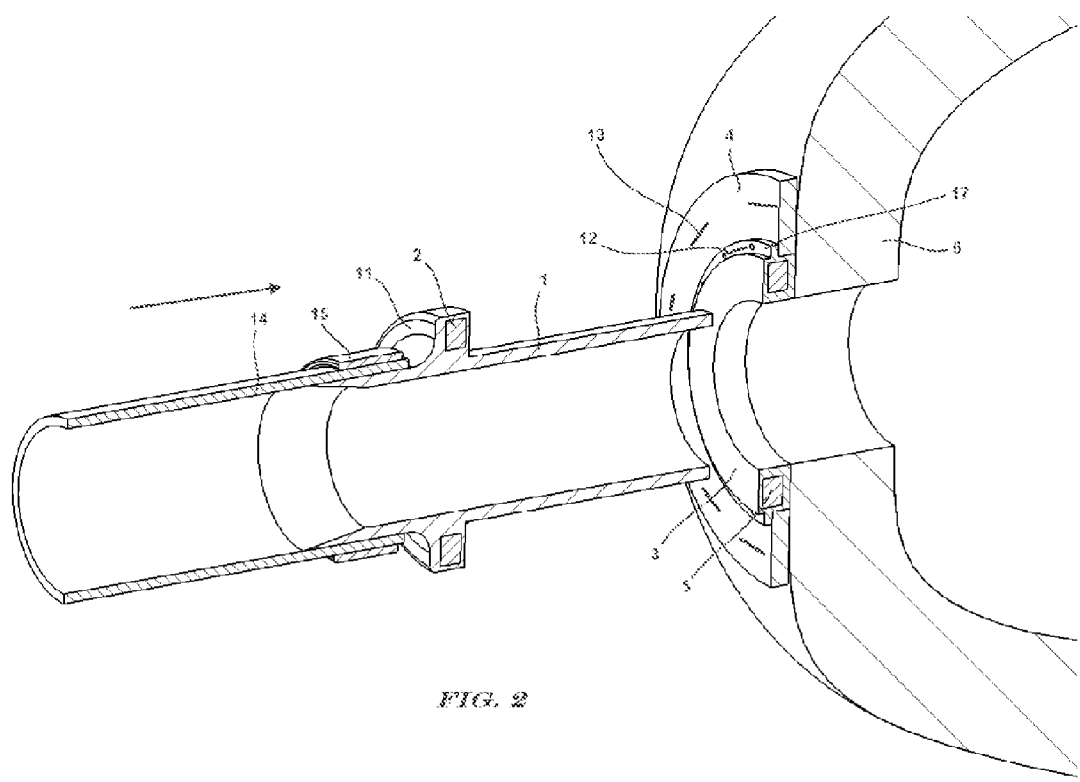
FIG. 2 is a perspective exploded sectional view showing the embedded magnet in the flange of the first member and the embedded magnet in the ring of the second member and the sewing ring attached to the second member.
Figure 3:
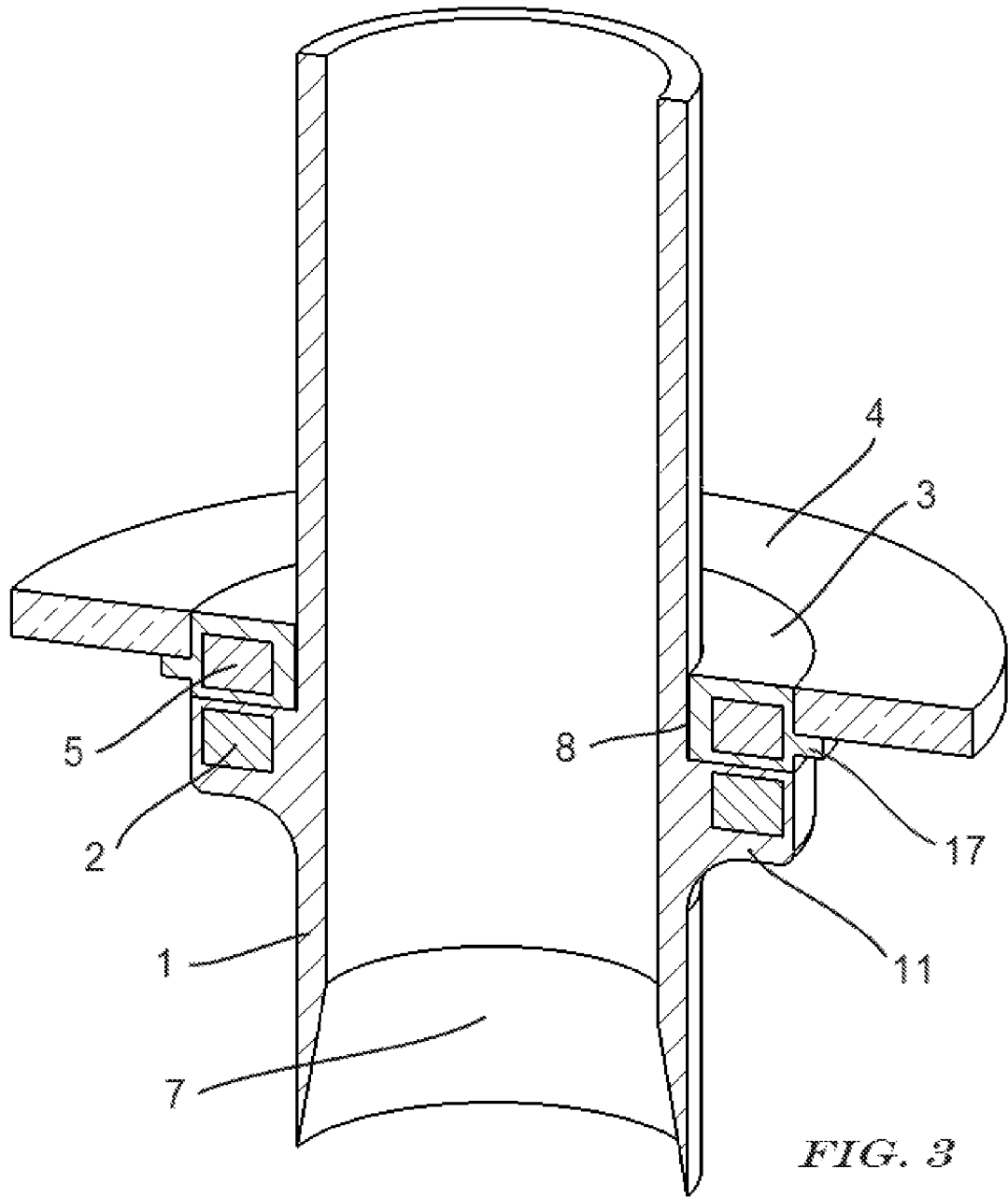
FIG. 3 is a perspective sectional view of the first and second members fully attached, and illustrating the proximity of the embedded magnets when fully assembled.

FIGS. 1-3 show a magnetic connector system 10 for attaching a cannula to a ventricle 6 of a heart. The connector system includes a first member 1 containing a first orifice 7 through which fluids may flow. In the illustrated embodiment, the first member 1 and orifice 7 form a tube, but it should be understood that other shapes could be utilized. A first magnetic material 2 is attached to the first member 1. The first magnetic material may be comprised of any type of permanent magnet or magnetically permeable material. The illustrated embodiment shows the first magnetic material 2 embedded into a flange 11 emanating from the outer wall of the first member 1 as the means for attachment, however it should be understood that various devices could be utilized for attaching the magnet to the first member, including fasteners, welding, adhesives, and slip and press fits. A second member 3 comprising a second orifice defined by an inner wall 8 (see FIG. 3) that is slightly larger than the outer diameter of the first member 1. A second magnetic material 5 attached to the second member by similarly various means and may be comprised of a range of materials similar to the first magnetic material 2. An attachment ring 4 attached to the second member 3 serves to attach the second member to the ventricle 6 of the heart, and may comprise a fabric such as polyester velour, felt, expanded polytetrafluoroethylene (EPTFE) or various other fabrics well known in the art. Sewing ring 4 is adapted for attachment to the heart 6 with sutures or staples 13 which penetrate the attachment device and the exterior wall of the heart. Attachment ring 4 may be attached to the second member 3 by various means including stitches, adhesives or various mechanical fasteners. As can be seen in FIG. 1, the second member 3 is attached to the ventricle 6 via the sewing ring 4. The first member 1 assembles onto the second member 3 by inserting the tubular portion of the first member 1 through the orifice in the second member 3 defined by the inner wall 8. In this position, the first magnetic material 2 is brought in proximity to the second magnetic material 5 and through magnetic force the first and second members are held substantially together so as to secure the first member 1 to the ventricle 6 and allow the communication of fluid through the first orifice 7 and the ventricle 6. It should be understood that a predefined attachment force as dictated by the strength and position of the magnetic materials relative to each other may be chosen such that a desired securing force can be achieved. It should also be understood that this force can be selected to enable detachment of the first member 1 from the second member 3 and thus ventricle 6 under a removal force.

In operation, when it is desired to attach a tube to the heart, the sewing ring 4, which has been pre-attached to the second member 3, may be sewn to the outer surface of the heart 6, as shown in FIG. 1. A hole is cored from the heart 6 substantially concentric with the orifice 8 of the second member 3. The tip of the first member 1 is then inserted through the orifice of the second member 3 and the hole that has been cored into the heart 6. The first member 1 is then advanced into the heart 6 until the flange 11 holding the first magnet 2 is brought into contact with the second member 3 holding the second magnet 5. The attractive force between the first 2 and second magnets 5 secures the first member 1 to the second member 3 which is secured to the heart by the sewing ring 4.

The present invention enables the attachment of a tube to the heart in a rapid one-handed motion which enables the ability of performing such maneuver off cardiopulmonary by-pass and without a clear visual field. If repositioning of the tube is desired, a force in excess of the attachment force of the two magnets can be applied and the tube easily removed, repositioned, and reattached without having to manipulate any other securing mechanism such as sutures, fasteners, or clamping screws as is common with the prior art. The illustrative embodiment further enables the rotation of the tube once it is within the heart so as to minimize twists in a cannula attached to the tube. This feature may be particularly significant to reduce problems when the cannula is attached to a blood pump.

Figure 4:
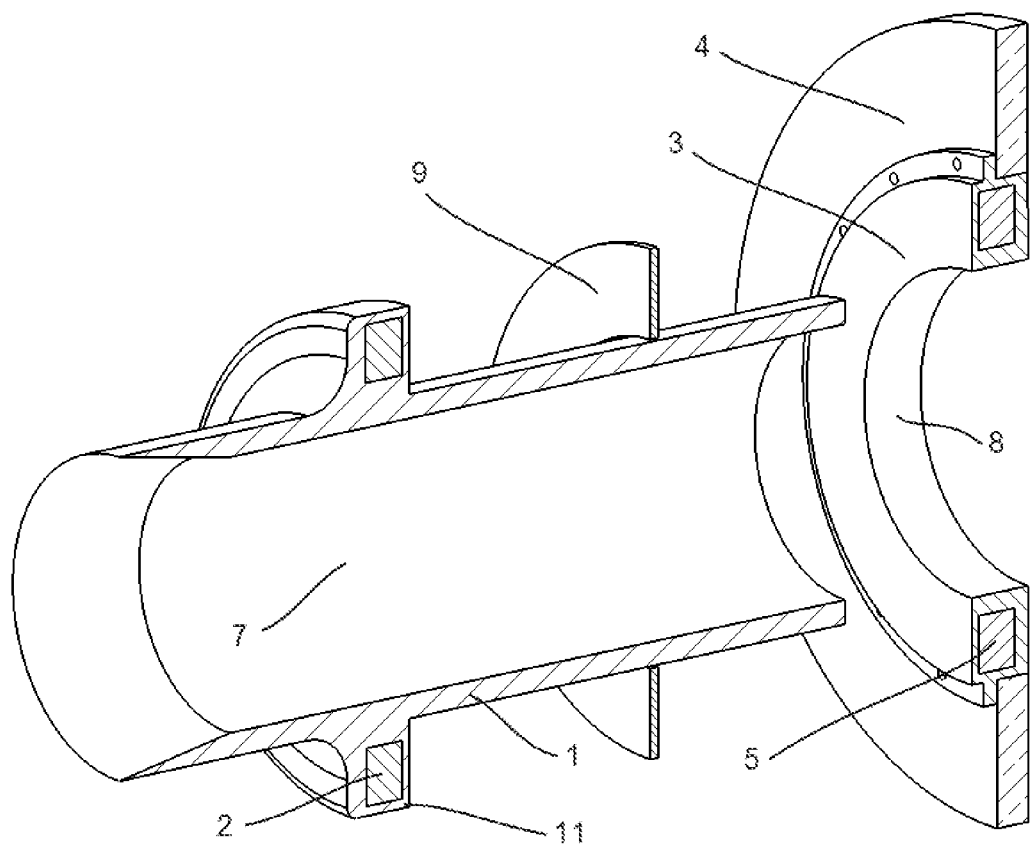
FIG. 4 is a perspective sectional exploded view showing the location of the silicone sealing washer between the first and second members.
Figure 5:
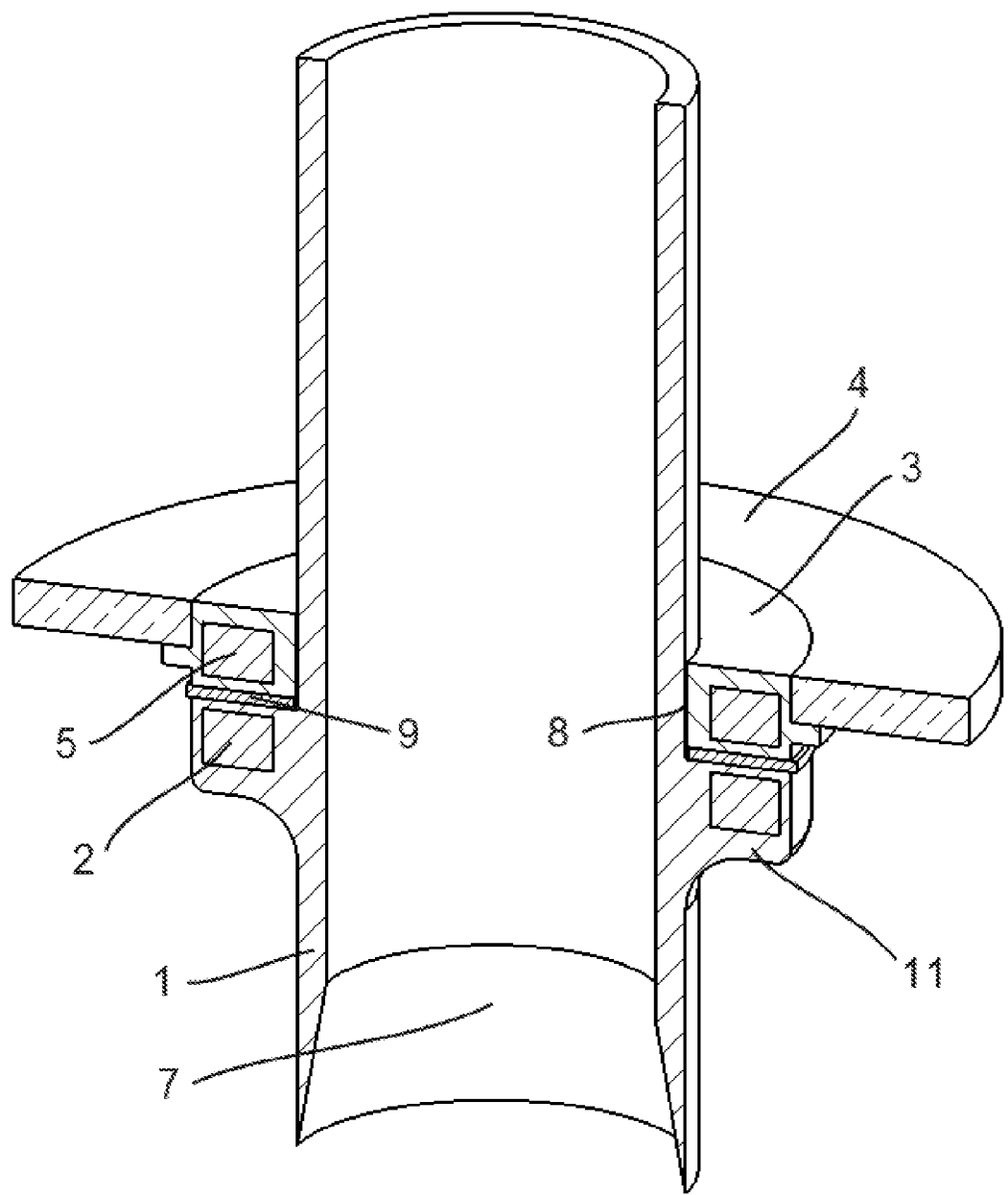
FIG. 5 is a perspective sectional view of the silicone washer sandwiched between the first and second members when they are fully assembled.
Figure 6:
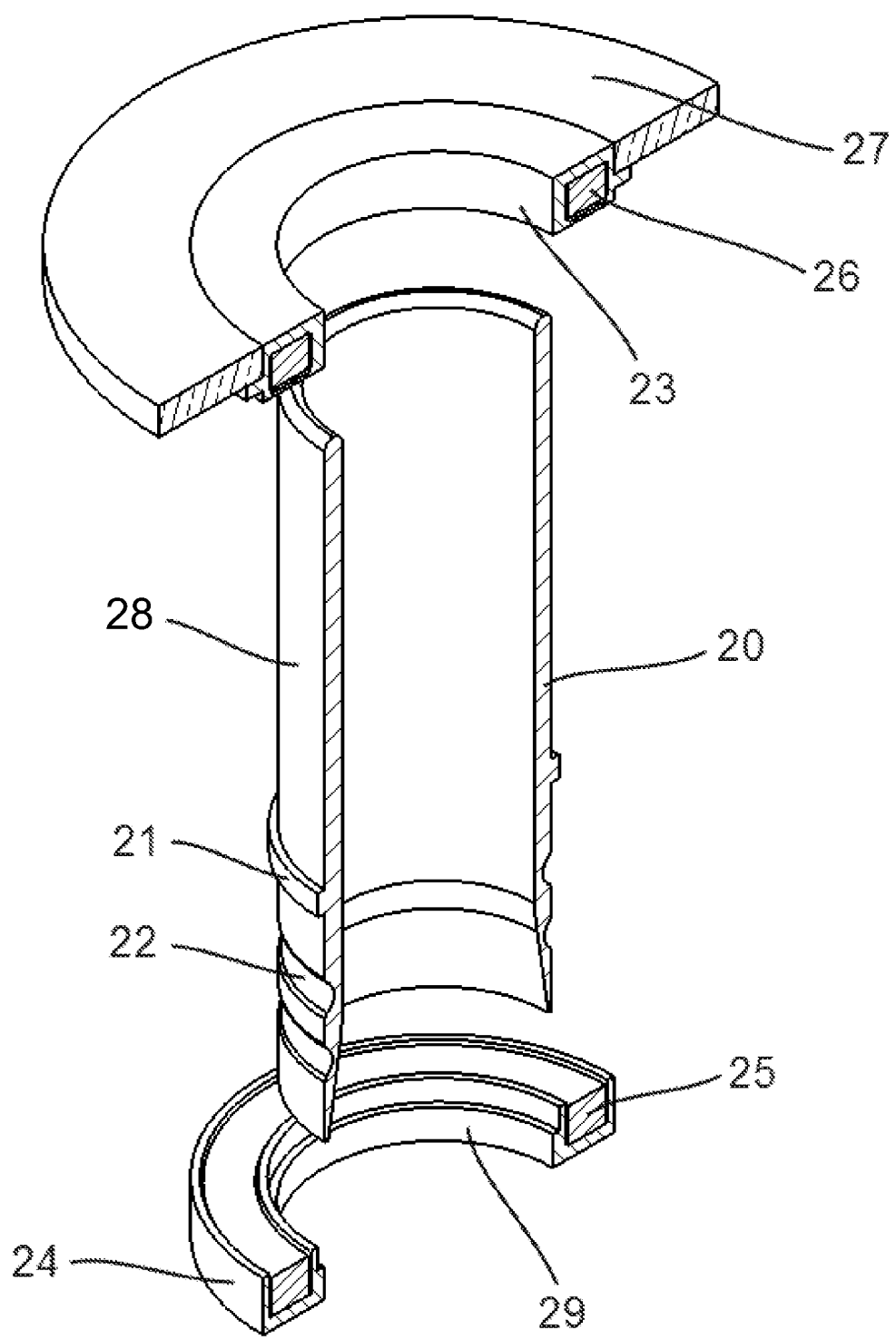
FIG. 6 is a perspective sectioned exploded view of an alternative embodiment showing the tube with raised circumferential abutment and grooves for attachment of a cannula, the second member, and the third member with an embedded magnet.

Referring now to FIGS. 4-5, a similar arrangement is illustrated with the addition of a sealing washer 9. The sealing washer can be comprised of various elastomeric sealing materials such as silicone. The sealing washer has an orifice through which the tubular portion of the first member communicates. Upon assembly (as shown in FIG. 6) the sealing washer is compressed between the flange 11 of the first member 1 and the second member 3 by the magnetic force between the first 2 and second 5 magnetic materials which draws the first 1 and second 3 members together. In this position, the sealing washer 9 can prevent fluid from traveling from the ventricle 6 around the outer wall of the tubular portion of the first member 1 and into the surrounding space.

In the embodiment as shown in FIGS. 4 and 5, a silicone washer 9 is located around the flange 11 of the first member at the plane that mates with the titanium ring 3 of the second member. When the first and second members are engaged, the silicone washer 9 is sandwiched between the first flange and the second ring thereby creating a seal to prevent substantial leakage of fluid.

Figure 7:
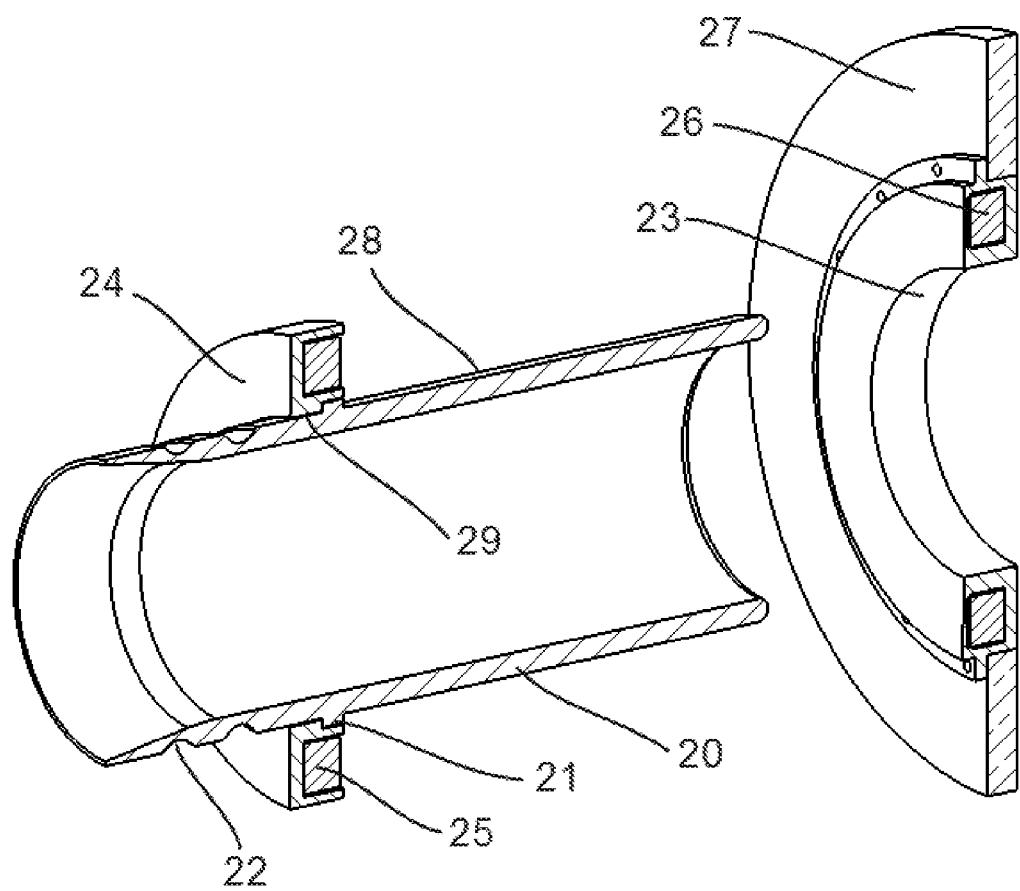
FIG. 7 is a perspective sectional view showing engagement of the third member with the abutment on the hollow tube.
Figure 8:
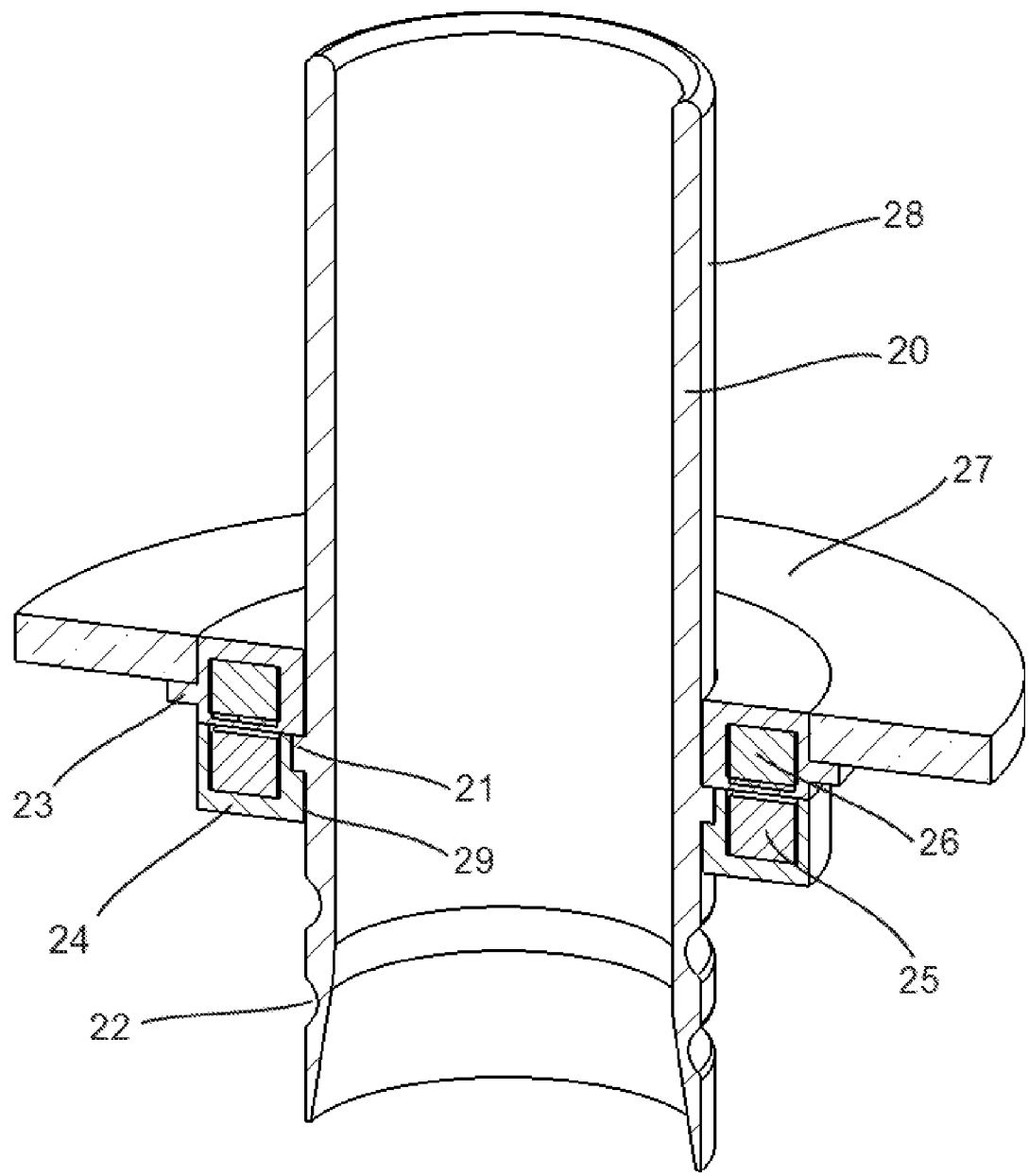
FIG. 8 is a perspective sectional view of the fully assembled alternative embodiment illustrating the location of the third member when engaging the hollow tube through the abutment and engaging the second member via magnetic interaction with the respective embedded magnets.

In an alternative embodiment as shown in FIGS. 6-8, the first member is a titanium tube 20 possessing a raised section 21 around the outer circumferential surface, and the raised section has a greater diameter than the rest of the tube so as to serve as a catch or stop. A second member may be identical to the one previously described. A third member 24 is comprised of titanium, has an orifice, and having an embedded permanent magnet 25. The orifice of the third member sized to slide freely over the normal section of the first member but to catch at the raised section of the first member. When assembled, the third member engages the first member and acts as a flange. When the assembled first and third member are inserted through the orifice of the second member, the embedded magnet in the third member engages the magnet in the second member attractively and thus holds the first member against the second member through engagement with the catch.

In FIGS. 6-8, the alternative embodiment shows a hollow tube 20 with a raised abutment or flange 21 around its outer wall 28. The tube may be comprised of titanium or similar hemocompatible material. The hollow tube comprises a plurality of grooves 22 located at its distal end for the purpose of securing a cannula to the tube with a plurality of ligatures. A ring 24 with an orifice defined by an inner wall 29 greater than the diameter of the outer wall 28 of the hollow tube 20 but less than the outer diameter of the raised abutment 21. The ring may be comprised of titanium or similar biocompatible materials. A magnet material 25 is attached to the ring 24. A second member 23 exists which has attached to its structure by the various means previously described a second magnet 26 and a sewing ring 27. The sewing ring material and magnetic material may be similar to those previously described. As shown in FIG. 7, upon assembly of the ring 24 and hollow tube 20, the inner wall of the ring 29 does not interfere with the outer wall 28 of the hollow tube, but interferes with the raised abutment 21, whose outer diameter is greater. In this manner, the abutment 21 acts as a stop to prevent the ring 24 from translating further along the hollow tube. Upon assembly of the ring 24 and hollow tube 20 with the second member 23 (FIG. 8), the first 25 and second 26 magnetic materials are brought into proximity and provide an attractive securing force between the hollow tube 20 and the second member 23 by transduction of force through the raised abutment 21.

Figure 9:
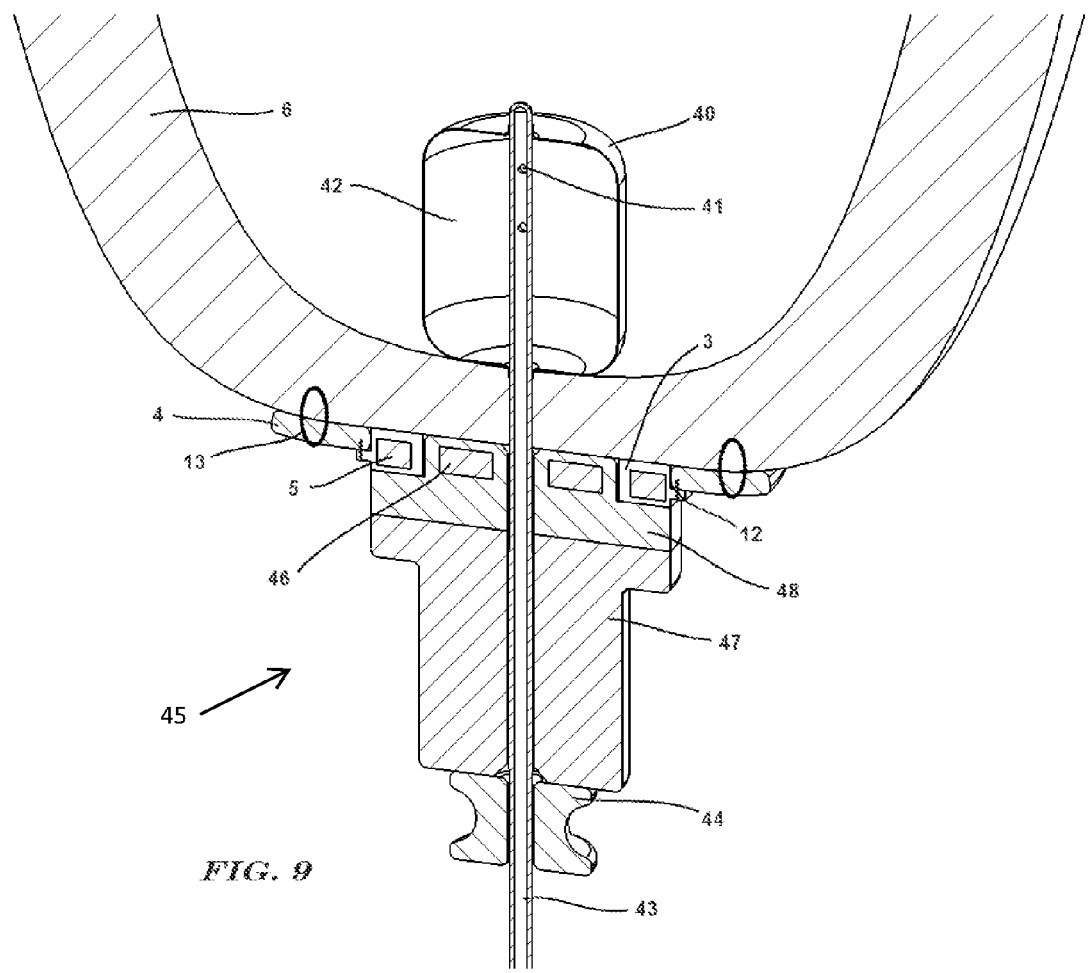
FIG. 9 illustrates a portion of a heart, a sewing ring, a balloon catheter, and a positioner.

FIG. 9 provides a means for visualizing the future orientation of an inflow cannula tip inside of the ventricle, thereby aiding proper alignment of the sewing ring so as to prevent the inflow tip from interacting with surfaces or structures inside of the heart (a common problem that results in thrombosis and or suction). After loading the second member 3 onto flux shield 48 and positioning the sub-assembly 45 as shown, the method includes first puncturing a hole in the ventricle and inserting a balloon tipped catheter 43 along the axis in which one wants the inflow tip to orient. The balloon membrane 40 is then inflated with radiopaque contrast passing through ports 41 and into the interior 42 of the balloon which is designed to inflate to the dimension of the future inflow tip, such that under X-ray the orientation of the future inflow tip can be directly visualized and obstructions observed. The use of contrast in the ventricle simultaneously or echocardiography may be used to enhance visualization of the balloon and ventricle. If the orientation is poor, the process can be repeated at a new orientation.

The positioner 47 may be attached by conventional securing members to a flux shield 48 with magnet 46 embedded therein. This sub-assembly is shown more clearly in FIG. 10 and may be referred to as a positioner sub-assembly 45. In many embodiments, the flux shield 48 is desirable for reasons explained subsequently. If positioner 47 were formed from a magnetically attractive material, the magnet 46 and shield 48 optionally may be deleted. In still other embodiments, a positioner magnet may be included within the body of positioner 47 and shield 48 eliminated. In a preferred embodiment, however, the shield 48 is utilized in the FIG. 9 assembly, and may be fabricated from magnetic steel with magnet 46 therein.

The system in FIG. 9 positions a suture cuff or attachment ring 4 onto the ventricle in the predetermined orientation by using the axis of the balloon tip catheter as a guide. This orientation is ensured by using a positioner 47 that is magnetically coupled to the second member 3, the positioner 47 having a hole that accepts the rigid portion of the balloon tipped catheter 43. A friction nut 44 or similar device allows the sewing ring 4 to be compressed against the heart surface by sliding the positioner along the catheter until the sewing cuff or attachment ring 4 engages the heart surface. Once in place, the friction nut 44 prevents the positioner from sliding back unless substantial force is applied. In this fashion, the suture cuff is held in place without the use of hands and is ensured to guide the inflow tip along the same axis that was visualized previously by the balloon tip. Surgical tools and needles are typically comprised of 400 series stainless steel which is substantially magnetically attractive. The system may shield the magnetic field emanating from the suture cuff so as to prevent needles and surgical instruments from sticking to the magnetic coupling, as explained subsequently.

Once the sewing cuff 4 is stitched to the heart, the balloon may be deflated and removed from the heart. The subassembly 45 may be disengaged from the second member 3 and removed as well in preparation for coring the hole in the ventricle. During the coring procedure, the second member 3 serves as a guide and may magnetically engage the coring tool so as to ensure proper orientation. The inflow tip has a magnetic ring that engages the magnetic portion of the sewing ring to hold the cannula tip in place during normal use of the device.

If the pump needs to be explanted (in the case of reverse remodeling leading to cardiac recovery), the magnetic coupling provides a quick and easy means for disengaging the inflow tip from the heart. In its place, a magnetic plug can be easily engaged to the magnetic portion of the sewing ring to plug the hole and prevent blood from leaking from the ventricle.

Figure 10:
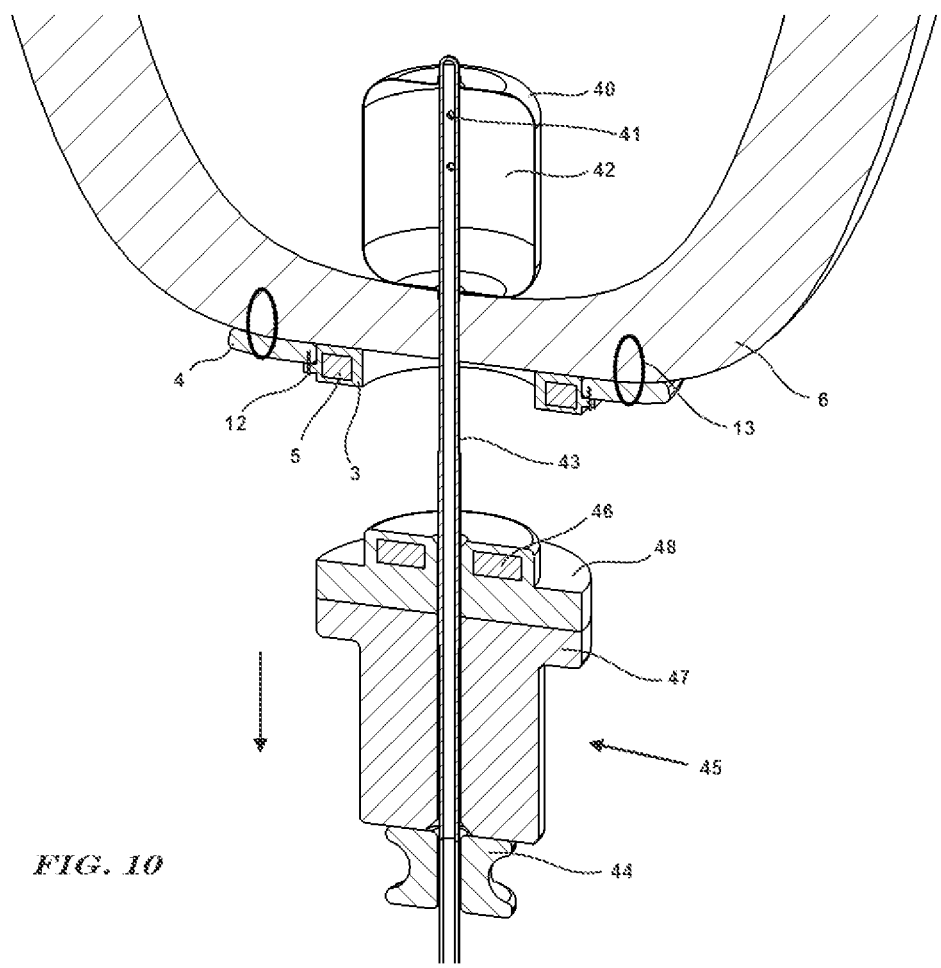
FIG. 10 illustrates the positioner being detached from the sewing ring in FIG. 9.

FIG. 10 illustrates a sewing cuff 4 with stitches 13 securing the sewing cuff to the heart. With the balloon catheter in place, the positioner 47, flux shield 48 discussed subsequently, and friction nut 44 may be removed as a sub-assembly 45 by pulling the sub-assembly toward the rear or distal end of the catheter.

Figure 11:
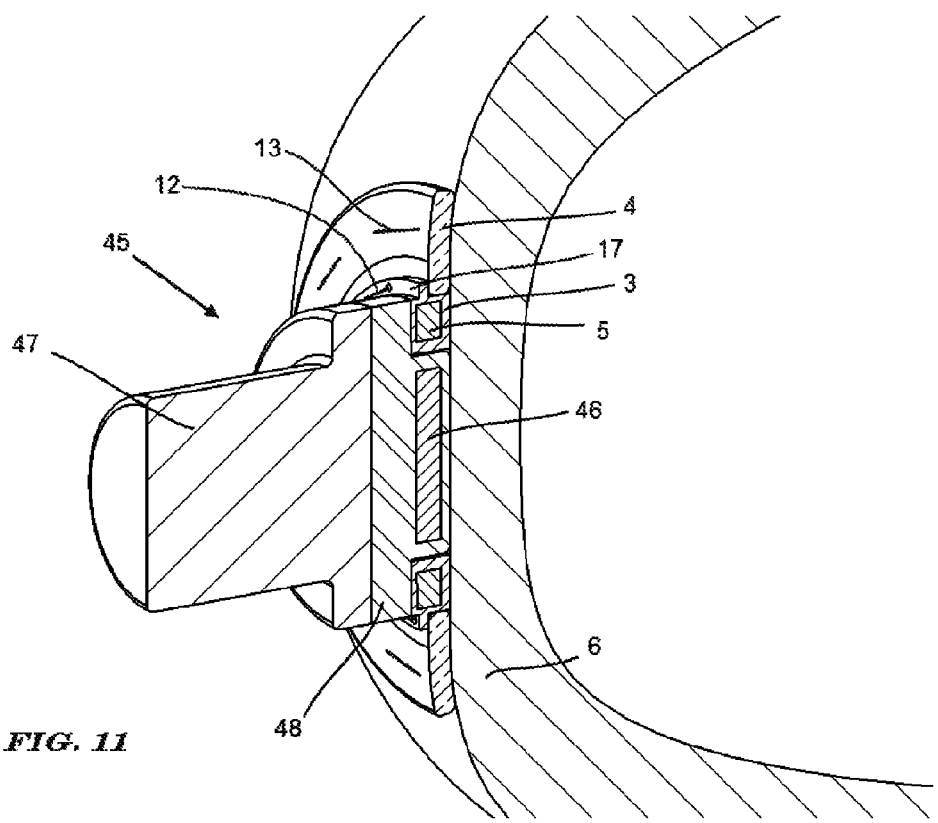
FIG. 11 illustrates the sewing ring, a positioner, and a flux shield.

FIG. 11 shows a sewing ring positioner 47 and a modified sub-assembly magnetically attached to the second member 3 and positioned against the surface of a heart 6. Magnet 46 may be positioned within flux shield 48. The positioner 47 and flux shield 48 thus may or may not include a positioner magnet 46. The flux shield 48 may be comprised of a variety of magnetically permeable materials, such as steel. The magnet 46 is shown attached to the flux shield 48 and in the preferred embodiment is embedded in the flux shield 48 so as to protect it from corrosion. The positioner magnet 46 provides an attractive force between the second member 3 and the sub-assembly 45 so that the sewing ring can be positioned using the sub-assembly 45. The flux shield 48 and positioner magnet 46 are thus attached to the positioner 47, which may be comprised of various non-ferromagnetic materials, such as plastic. When the flux shield 48 is assembled onto the second member 3, the flux shield 48 substantially redirects the magnetic flux generated by the second magnetic material 5 so as to prevent the fields from either magnet from interacting with surgical tools that fall within a close proximity of the positioner 47. The sub-assembly 45 as shown in FIG. 11 may be used to properly attach the sewing ring 4 and second member 3 to the heart prior to coring a hole through the opening in the second member for passing the first member through the second member and into the heart.

Figure 12:
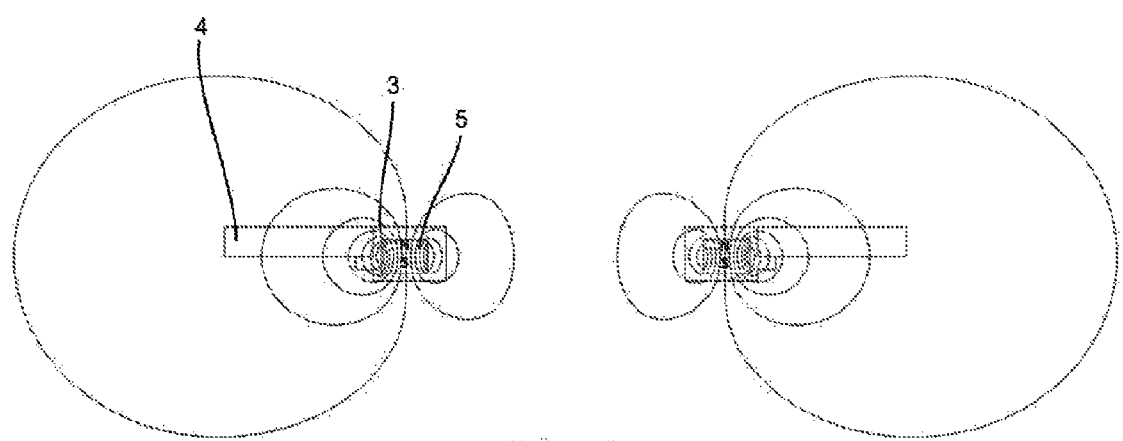
FIG. 12 illustrates a side view of the magnetic field generated by the sewing ring magnet.
Figure 13:
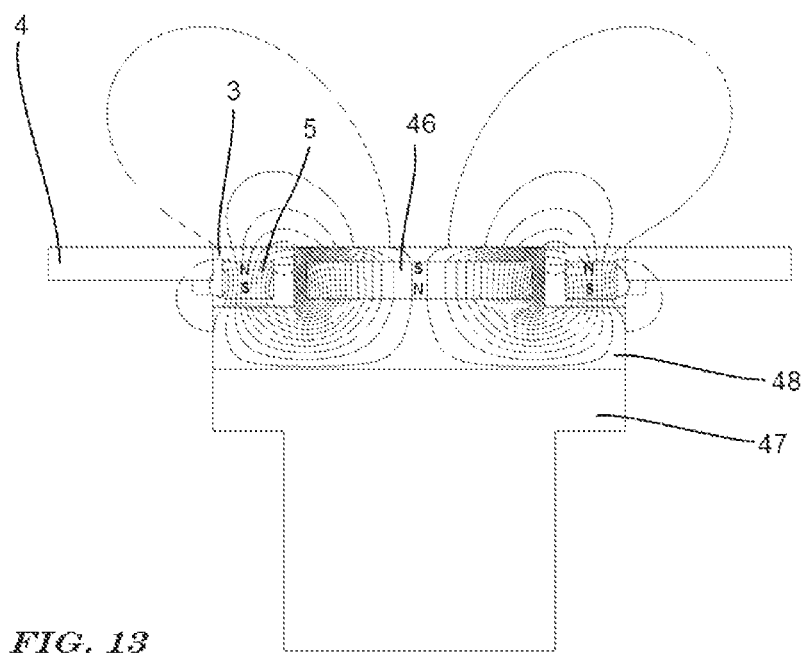
FIG. 13 is a side view of the redirected magnetic field due to the magnetic flux shield.

FIG. 12 illustrates the magnetic field generated by the second magnetic material 5. This magnetic field can attract surgical tools and needles used to secure the sewing cuff 4 onto the outer surface of the heart 6. FIG. 13 shows the result of redirection of the magnetic field by the magnetic flux shield 48.

FIGS. 12 and 13 illustrate how the magnetic field produced by the magnet in the second member is affected by the flux shield 48, which may be magnetically permeable material. In FIG. 12, the field produced by the magnet 5 is radially symmetric, so each side contains similar information. FIG. 12 shows the magnetic field that is produced solely by magnet 5. FIG. 12 thus shows the field that would be encountered if the sewing ring were to be sewn to the heart without the positioner and the flux shield in place. Surgical tools would commonly be manipulated in the area beneath the sewing ring, and would pass into flux lines so that the tools would become attracted to magnet 5.

The flux shield 48 as shown in FIG. 13 ducts the field lines produced by magnets 46 and 5 so that field lines do not extend into the area in which surgical tools would be working. FIG. 13 is the resultant field of both magnets 46 and 5 interacting in the presence of the flux shield. With the positioner in place, the field lines are thus ducted out of this surgical area by the flux shield. In FIG. 13, the flux shield 48 effectively redirects the field of the magnet to prevent the magnet from interacting with surgical tools or other permeable material that might come into proximity of the sewing cuff, and particularly permeable material directly below sewing cuff 4 or adjacent the sides of either the flux shield 48 or the top of the positioner 47.

Figure 14:
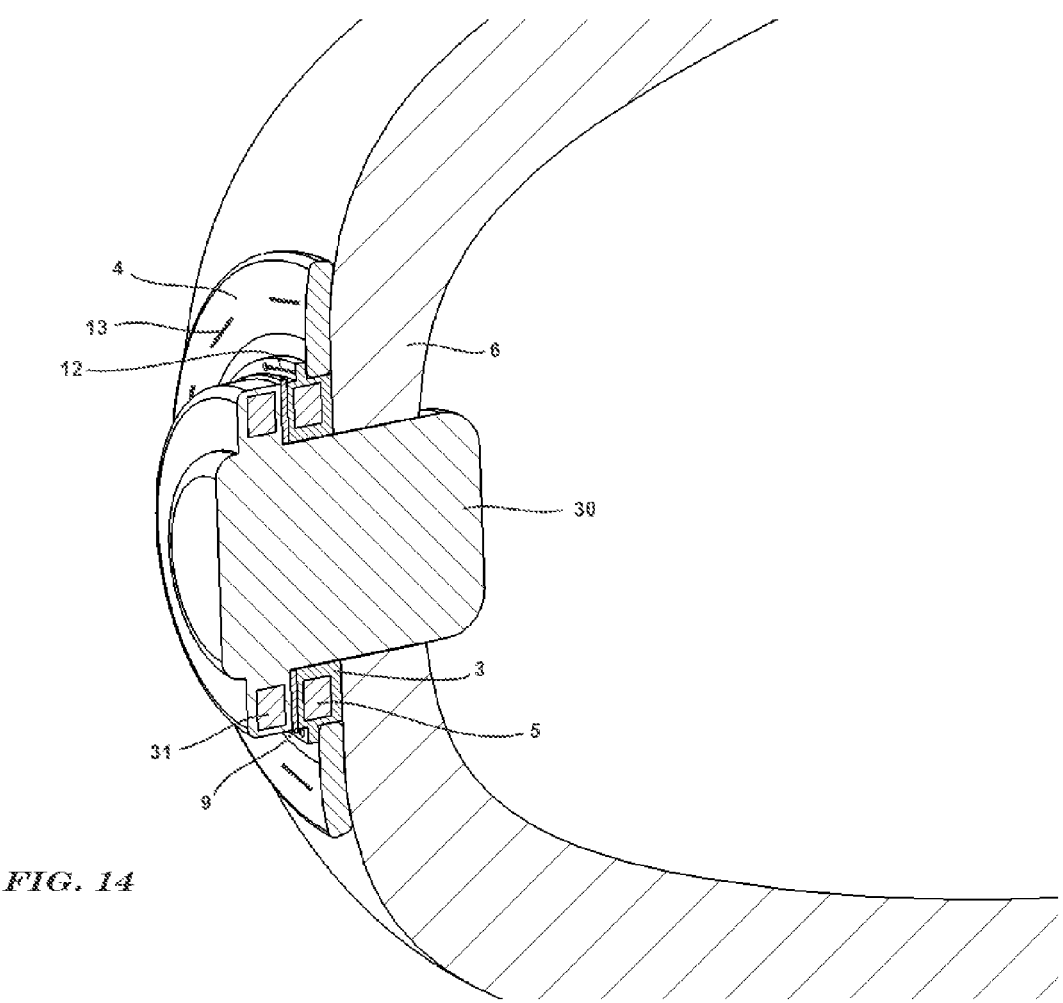
FIG. 14 illustrates a plug for plugging the hole in the ventricle.

In FIG. 14, a magnetically attached sealing plug 30 with plug magnet 31 seals the hole in the ventricle using the previously attached sewing ring. The sealing plug 30 is shown magnetically coupled to the second member 3. The plug 30 may be comprised of a variety of hemocompatible materials, such as titanium or stainless steel. A plug magnet 31 is attached to the plug 30, and in the preferred embodiment supplies an axially directed magnetic attachment force between the plug 30 and second member 3 when the plug 30 is inserted through the second member 3 and the magnets 31 and 5 are brought into proximity of each other. One function of the plug 30 is to occlude the opening in the ventricular wall 6 after removal of a previously residing cannula as would occur in the case of removal or replacement of a ventricular assist device. Upon assembly onto the second member 3, the plug 30 compresses the sealing washer 9 via the axial magnetic connection force, sealing off the pathway for blood to leak between the plug 30 and second member 3. The plug 30 substantially limits blood from flowing out of the hole and provides a structure for fibrotic tissue to further seal off the previous wound. The plug 30 is designed to magnetically couple to the previously used second member 3 so as to provide a quick and easy method for sealing off the coring hole.

Two similar magnets may be used to attract and hold one member relative to the attachment ring. In another embodiment, one of the magnets may be replaced with a magnetically attractive ring, such as a steel ring, so that it is attracted to the other magnet. If only one magnet is used, it preferably is provided in the attachment ring, since that ring generally remains in place to cooperate with a mating member. The holding strength of the two magnet embodiment should generally be greater than a single magnet embodiment. As used herein, a "magnetic material" means a magnet or a magnetically permeable material, and thus includes, for example, permanent magnets or one permanent magnet and steel.

A method of attaching the inflow cannula of a ventricular assist device to the heart using a magnetic sewing ring and balloon catheter is set forth below:

1. Determine the entry point and the desired axis in which the inflow cannula should reside. The inflow cannula should point towards the mitral valve and should not angle towards or impinge upon any wall of the heart. Care should be taken to avoid positioning or angling the cannula towards an endocardial surface since wall suction events may occur during aspiration of the pump if the inflow orifice is sufficiently close to an endocardial surface. Repeated suction events can cause trauma to the heart and significantly diminish pumping support.

2. Administer systemic anticoagulation.

3. Use a large bore needle to make an insertion through the wall of the heart along the chosen axis. Remove the needle.

4. Insert the balloon catheter through the hole that was created by the needle and push until the balloon is inside of the ventricle. Use an introducer if needed. The balloon is deflated at this stage. The balloon catheter comprises a rigid section at the insertion end that facilitates insertion of the catheter through the ventricular wall, and serves as a rigid guide for future alignment of the sewing ring. The distal portion of the catheter is flexible to allow for manipulation. The distal tip of the balloon catheter comprises a silicone plug that acts as a low profile seal that still allows for instruments to be slid over the catheter.

5. Using a syringe with a small needle, insert the needle through the silicone plug and inflate the balloon catheter with radiopaque contrast dye.

6. Pull on the catheter until the balloon engages the apical endocardial surface.

7. Using x-ray or a fluoroscope,—visualize the balloon in the ventricle. Additional contrast may be injected into the ventricle to visualize the ventricular margin. The balloon is designed to inflate to the same dimensions of the inflow cannula, thereby allowing visualization of the future inflow tip orientation prior to apical coring. Inspect the angle of the balloon to ensure proper positioning and inspect for papillary muscle or chordae that might pose a problem.

8. If the orientation is sufficient, proceed to the next step. If a problem with the position is observed, deflate the balloon and remove from the ventricle by applying traction to the catheter and then repeat at step 1 with a new orientation. The ability to check the inflow tip orientation prior to coring and inserting the inflow tip is a particular feature of this method.

9. Once the axis has been verified to be adequate, load the sewing ring onto the sewing ring positioner by aligning concentrically and engaging their respective magnets. Insert the free catheter end through the hole in the positioner and slide the positioner up the catheter until the sewing ring touches the heart surface. The positioner should be on the rigid portion of the catheter in this location and thus held along the predetermined axis. The friction nut should provide sufficient braking force to prevent the positioner from sliding back down the catheter. If additional frictional force is needed, a suture may be tied around the friction nut to increase its compression onto the catheter.

10. With the sewing ring now in place on the heart surface, stitch the sewing ring to the heart using interrupted purse string mattress sutures.

11. Once the sewing ring is sutured to the heart, remove the positioner by applying axial force to the positioner while holding the sewing ring to the heart surface so as not to put too much stress on the newly sutured connection. The positioner should magnetically disengage with the sewing ring and may be removed by sliding down the catheter.

12. Deflate the balloon by reinserting a syringe into the silicone plug and aspirating the contrast dye from the balloon.

13. Remove the balloon by gently applying traction to the catheter and pulling through the original needle hole in the ventricle.

14. Use a scalpel or multi-bladed tool to incise the ventricle where it appears at the center of the sewing ring. Upon removal of the scalpel, use a gloved finger over the wound to maintain hemostasis.

15. Advance the coring tool through the incision and core the ventricle

16. Remove the cored muscle and use a finger to cover the hole so that hemostasis is maintained.

17. Quickly remove finger and insert the inflow tip of the VAD cannula until the magnetic member of the inflow tip engages the magnetic member of the sewing ring, securing the inflow cannula to the apex. Once magnetic engagement occurs, check for any twists in the inflow cannula and rotate the inflow tip to correct.

Those skilled in the art will appreciate that the embodiments disclosed herein achieve the objective of quickly and reliably coupling one member to another so that blood may flow through the coupling to or from the heart. A feature of the various embodiments is a flexible attachment ring or sewing ring which is attached to the heart and has an opening for receiving at least a portion of another member therein, such that a tubular member may be inserted through the aperture in the attachment ring and into the heart. The blood flow to and from the heart may be easily and reliably controlled, and a substantially sealed connection to the heart may be quickly and easily made by the surgeon. In other embodiments, a flux shield is provided so that metal objects used during the surgery are not strongly attracted to the attachment ring.

Although specific embodiments of the invention have been described herein in some detail, this has been done solely for the purposes of explaining the various aspects of the invention, and is not intended to limit the scope of the invention as defined in the claims which follow. Those skilled in the art will understand that the embodiment shown and described is exemplary, and various other substitutions, alterations and modifications, including but not limited to those design alternatives specifically discussed herein, may be made in the practice of the invention without departing from its scope.

What is claimed is:

1. An angularly orientable magnetic connector system for attaching a cannula to a heart for passing blood into or from a chamber within the heart, the magnetic connector system, comprising:
 a first member having an inflow tip at a proximal end, a distal end and a first orifice;
 a second member having a second orifice sized to receive the inflow tip of the first member therethrough;
 a first magnetic material attached to the first member intermediate the inflow tip and the distal end and having an opening aligned with the first orifice of the first member;
 a second magnetic material attached to the second member and having an opening, such that the opening of the first magnetic material attached to the first member is aligned with the opening of the second magnetic material attached to the second member and the first magnetic material attached to the first member is magnetically attracted to the second magnetic material attached to the second member upon receiving the inflow tip of the first member through and beyond the second orifice of the second member; and a flexible attachment ring secured at a central opening in the attachment ring to the second member for attaching the second member to an exterior wall of the heart;

wherein the inflow tip of the first member is insertable in, and then magnetically securable beyond, the second orifice of the second member using a single hand;

wherein insertion of the inflow tip of the first member into the second orifice of the second member guides the first magnetic material attached to the first member to a magnetically coupled position proximal to and aligned with the second magnetic material of the second member;

wherein the inflow tip of the first member is angularly orientable relative to the attachment ring of the second member after the attachment ring is attached to the heart by rotation of the first member about an axis through the first orifice; and wherein unwanted twists in a flexible cannula connected to the distal end of the first member can be eliminated by angularly orienting the first member, to which the cannula is connected, relative to the second member.

2. The magnetic connector system of claim 1, wherein the first member comprises:

a flange intermediate the inflow tip and the distal end of the first member and extending radially outwardly from the first member.

3. The magnetic connector system of claim 2, wherein the first magnetic material is embedded within the flange on the first member.

4. The magnetic connector system of claim 2, wherein the second member comprises:

a flange extending radially outwardly from the second member.

5. The magnetic connector system of claim 1, further comprising:

a sealing member between an exterior surface of the first member and the second orifice of the second member.

6. The magnetic connector system of claim 1, wherein the flexible attachment ring for attaching the second member to the exterior wall of the heart comprises a sewing ring.

7. The magnetic connector system of claim 1, further comprising:

one or more circumferential grooves in an exterior surface of the distal portion of the first member for sealably attaching the cannula to the distal portion of the first member.

8. The magnetic connector system of claim 1, further comprising:

a balloon catheter for passing through the orifice of the second member and into the heart; and a positioner, including a positioner magnet disposed on a portion of the balloon catheter for cooperating with the second magnetic material attached to the second member and for thereby positioning the balloon catheter relative to the second member.

9. The magnetic connector system of claim 1, further comprising:

a plug, including a magnetic material that is attracted to the second magnetic material of the second member, and substantially occluding a hole in the heart when the first member is removed from the second member and the plug is received within and magnetically coupled to the second member.

10. The magnetic connector system of claim 1, further comprising:

a flux shield to alter a magnetic field produced by the second magnetic material of the second member to reduce the magnetic force imparted to metal objects positioned adjacent to the second magnetic material.

11. An orientable magnetic connector system for attaching a cannula to a heart for passing blood into or from a chamber of the heart, comprising:

a hollow tube having an inflow tip at a proximal end and a distal end, a first outer diameter and a raised circumferential abutment intermediate the inflow tip and the distal end and having a second outer diameter that is greater than the first outer diameter of the hollow tube;

a first member ring with a first orifice having a diameter that is greater than the first outer diameter of the hollow tube but less than the second outer diameter of the raised circumferential abutment of the hollow tube;

a first magnetic material having an opening and attached to the first member ring with the opening aligned with the first orifice of the first member ring and with the opening of the first magnetic material having a diameter that is greater than the first outer diameter of the hollow tube;

a second member with a second orifice having, a diameter that is greater than the first outer diameter of the inflow tip of the hollow tube;

a second magnetic material having an opening that is larger than the diameter of the inflow tip of the hollow tube and attached to the second member with the opening of the second magnetic material aligned with the second orifice of the second member; and an attachment member for attaching the second member to an exterior wall of the heart;

wherein the inflow tip of the hollow tube is insertable in, and then magnetically securable at a position beyond, the second orifice of the second member using a single hand;

wherein insertion of the inflow tip of the hollow tube into the second orifice of the second member guides the first magnetic material attached to the first member ring to a magnetically coupled position proximal to and aligned with the second magnetic material of the second member;

wherein the inflow tip of the hollow tube is angularly orientable relative to the attachment ring of the second member after the attachment ring is attached to the heart; and wherein unwanted twists in a flexible cannula connected to the distal end of the hollow low tube can be eliminated by angularly orienting the hollow tube to which the cannula is connected relative to the second member.

12. The magnetic connector system of claim 11, further comprising:

a seal between the abutment of the hollow tube and the second member.

13. The magnetic connector system of claim 11, further comprising:

a balloon catheter insertable into a chamber of the heart and having flow bore through which contrast dye may flow; and a positioner, including a positioner hole, to receive and align the balloon catheter and to provide for translation of the positioner over the balloon catheter, and a positioner magnet for cooperating with the second magnetic material attached to the second member and to retain the balloon catheter in a position aligning the positioner magnet with the second magnetic material.

14. The magnetic connector system of claim 11, wherein the first magnetic material is embedded in the first member ring.

15. The magnetic connector system of claim 11, further comprising:
a plug including a magnetic material that is attracted to the second magnetic material of the second member, the plug substantially occluding a hole in the heart when the first member is removed from the second member and the plug is magnetically coupled to the second member.

16. The magnetic connector system of claim 11, further comprising:
a flux shield to alter a magnetic field produced by the second magnetic material of the second member to reduce the magnetic force imparted to metal objects positioned adjacent to the second magnetic material.

17. A method of connecting a cannula to a chamber of a heart, the method comprising:
providing a first member having a hollow tube with an inflow tip, a distal end, a first orifice and a first flange;
providing a second member having a second orifice, an attachment ring and a second flange;
attaching a first magnetic material to the first member proximal to the first flange of the first member;
attaching a second magnetic material to the second member and proximal to the second flange of the second member such that the first magnetic material proximal to the first flange of the first member is magnetically attracted to the second magnetic material proximal to the second flange of the second member upon alignment of the first magnetic material with the second magnetic material;
attaching the attachment ring of the second member to an exterior wall a heart using ligatures;
using a single hand to introduce the inflow tip of the first member into the second orifice in the second member to align the first magnetic material attached to the first member with the second magnetic material attached to the second member to cause the first magnetic material of the first member to be magnetically attracted to the second magnetic material of the second member;
translating the inflow tip of the first member through the second orifice of the second member to move the first flange of the first member to engage the second flange of the second member and to position the first magnetic material in close proximity to the second magnetic material;
connecting a proximal end of a cannula to the distal end of the first member; and
flowing a fluid through the cannula, the first orifice of the first member and the inflow tip.

18. The method of claim 17, further comprising:
passing an inflatable balloon catheter, having a collapsed configuration and an inflated configuration the size of the portion of the first member intermediate the inflow tip and the first flange, into a chamber of the heart and through the second orifice of the second member and into the heart;
providing a positioner including a positioner hole, for receiving the proximal end of the balloon catheter and for providing translation of the positioner over the balloon catheter, and a positioner magnet, for magnetically cooperating with the second magnetic material of the second member and for thereby positioning the second member relative to the balloon catheter;
introducing a volume of radiopaque material into the balloon catheter to inflate the balloon catheter from the collapsed configuration to the inflated configuration; and
using a radiation generating device to view the profile of the inflated balloon catheter to detect its position within the chamber of the heart relative to surrounding structures;
attaching the second member to the positioner by magnetic cooperation of the positioner magnet and second magnetic material;
inserting the proximal end of the balloon catheter into the positioner hole of the positioner; and
advancing the positioner along the balloon catheter until the second member reaches the surface of the heart, thereby aligning the second member with the balloon catheter.

19. The method of claim 18, further comprising:
inflating the balloon catheter to a predetermined shape corresponding to the portion of the first member inserted through the second orifice.

20. The method of claim 17, further comprising:
providing a plug including a magnetic material that is magnetically attracted to the second magnetic material of the second member;
removing the first member from engagement with the second member; and
engaging the plug with the second member to occlude the second orifice of the second member to prevent flow through a hole in the heart wall adjacent to the second member.

* * * * *